(12) United States Patent
Majeed et al.

(10) Patent No.: US 9,498,423 B2
(45) Date of Patent: *Nov. 22, 2016

(54) SYNERGISTIC SELENOPEPTIDE FORMULATIONS FOR THE PROTECTION OF DERMAL PAPILLA CELLS

(75) Inventors: Muhammed Majeed, Edison, NJ (US); Kalyanam Nagabhushanam, East Windsor, NJ (US)

(73) Assignee: Sami Labs Limited, Bangalore (IN)

( * ) Notice: Subject to any disclaimer, the term of this patent is extended or adjusted under 35 U.S.C. 154(b) by 226 days.

This patent is subject to a terminal disclaimer.

(21) Appl. No.: 13/465,873

(22) Filed: May 7, 2012

(65) Prior Publication Data
US 2013/0295668 A1    Nov. 7, 2013

(51) Int. Cl.
| | | |
|---|---|---|
| *C12N 5/07* | (2010.01) | |
| *A61K 8/60* | (2006.01) | |
| *A61K 8/64* | (2006.01) | |
| *A61Q 17/00* | (2006.01) | |
| *A61K 8/97* | (2006.01) | |
| *A61K 8/368* | (2006.01) | |
| *A61Q 17/04* | (2006.01) | |
| *A61K 36/889* | (2006.01) | |
| *A61K 38/05* | (2006.01) | |

(52) U.S. Cl.
CPC .............. *A61K 8/60* (2013.01); *A61K 8/368* (2013.01); *A61K 8/64* (2013.01); *A61K 8/97* (2013.01); *A61K 36/889* (2013.01); *A61K 38/05* (2013.01); *A61Q 17/00* (2013.01); *A61Q 17/04* (2013.01)

(58) Field of Classification Search
CPC ............ A61K 8/60; A61K 8/64; A61K 8/97; A61K 38/899; A61K 38/05; A61K 8/358; A61Q 17/00; A61Q 17/04
See application file for complete search history.

(56) References Cited

U.S. PATENT DOCUMENTS

| | | | | |
|---|---|---|---|---|
| 8,003,614 | B2 * | 8/2011 | Majeed et al. | 514/21.91 |
| 8,193,156 | B1 * | 6/2012 | Majeed et al. | 514/21.91 |
| 8,247,003 | B2 * | 8/2012 | Majeed et al. | 424/725 |
| 2006/0240126 | A1 * | 10/2006 | Majeed et al. | 424/702 |
| 2008/0026017 | A1 * | 1/2008 | Majeed et al. | 424/401 |
| 2010/0062989 | A1 * | 3/2010 | Majeed et al. | 514/25 |
| 2011/0003773 | A1 * | 1/2011 | Kepley et al. | 514/77 |
| 2011/0020814 | A1 * | 1/2011 | Dimos et al. | 435/6 |
| 2011/0033565 | A1 * | 2/2011 | Majeed et al. | 424/769 |

OTHER PUBLICATIONS

Hunt et al. Stem Cells (2008) 26: 163-172.*

* cited by examiner

*Primary Examiner* — Susan Hanley
(74) *Attorney, Agent, or Firm* — Oliff PLC

(57) ABSTRACT

The present invention discloses selenium peptide based synergistic compositions for the protection (morphology and viable numbers) of dermal papilla cells. The synergistic compositions disclosed in the present invention comprise (a) 1-O-galloyl-β-D-glucose (β-glucogallin) or 1-O-galloyl-β-D-glucose (β-glucogallin) and gallates (b) concentrate of liquid endosperm of *Cocos nucifera* and (c) selenopeptides.

18 Claims, 10 Drawing Sheets

Increasing dosages of UV (J/cm$^2$)

Row I: Untreated cells

Row II: PC-1 treated cells

Sample: PC-1

UVB = 0.648 J/cm²

Cell damage

Sample: PC-3

UVB = 0.648 J/cm²

No Cell damage

Sample: PC-3

UVB = 0.8 J/cm²

Cell damage/death

Sample: PC-2
UVB = 0.648 J/cm$^2$

Cell damage

Sample: PC-4
UVB = 0.648 J/cm$^2$

No Cell damage

Sample: PC-4
UVB = 0.8 J/cm$^2$

Cell damage/death

Sample: PC-3
UVB = 0.8 J/cm$^2$

Cell damage

Sample: PC-5
UVB = 0.8 J/cm$^2$

Cells Protected from damage

Sample: PC-3  
UVB=0.8 J/cm²

Sample: PC-6  
UVB= 1.0 J/cm²

Cell damage

Cells Protected from damage

Sample: PC-4
UVB = 0.8 J/cm²

Cell damage

Sample: PC-7
UVB = 0.8 J/cm²

Cell Protection from damage

Sample: PC-4
UVB = 0.8 J/cm²

Cell damage

Sample: PC-8
UVB = 1.0 J/cm²

Cell Protection from damage

FIG.10
FIG.10a
Sample: PC-9
UVB=0.432 J/cm$^2$
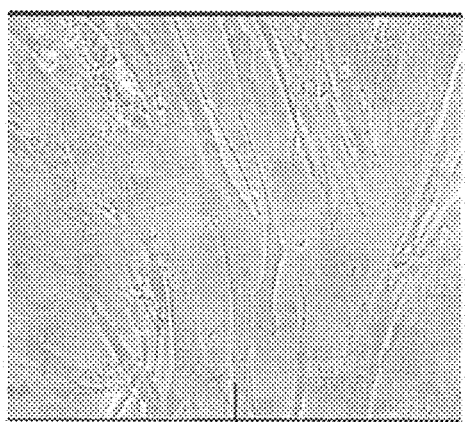
Cell Damage
FIG.10b
Sample: PC-9
UVB=0.432 J/cm$^2$
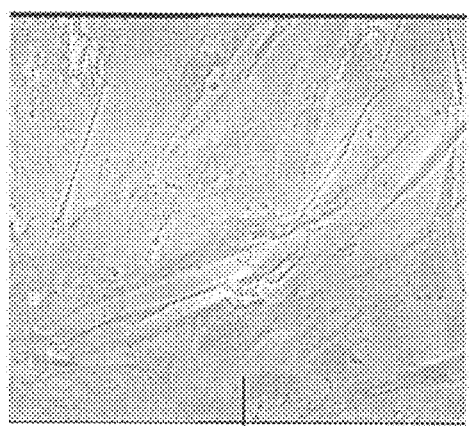
Cell Damage

SYNERGISTIC SELENOPEPTIDE FORMULATIONS FOR THE PROTECTION OF DERMAL PAPILLA CELLS

FIELD OF THE INVENTION

The present invention relates to protective compositions for dermal papilla cells. More specifically, the present invention relates to formulations comprising synergistic compositions that include (a) β-glucogallin or β-glucogallin and gallates, (b) concentrate of liquid endosperm of Cocos nucifera and (c) selenopeptides, for the protection of dermal papilla cells.

DESCRIPTION OF PRIOR ART

Dermal papilla cells are mesenchymal cells of the skin that not only regulate development of a hair peg but also constitute a reservoir of multi-potent stem cell lineages (Driskell et al., 2011). These stem cell lineages function as "tissue engineers" and are valued assets in regenerative medicine. Dermal papilla cells expressing the stem cell marker genes Sox 2 (transcription factor essential for the preservation of the pluripotent phenotype of stem cells) evince ability to self renew, induce hair peg formation and differentiate into fibroblasts that aid the formation of skin extracellular matrix. In fact, dermal papilla plays a very vital role in replacement of senescent fibroblasts with healthy ones thereby maintaining fibroblast numbers. Recent studies (Arnold I. Caplan, Diego Correa. The MSC: An Injury Drugstore. Cell Stem Cell, Volume 9, Issue 1, 11-15, 8 Jul. 2011 DOI: 10.1016/j.stem.2011.06.008) also indicate the role of mesenchymal stem cells (MSCs) as powerful "innate antidotes" in terms of their ability to (i) moderate unwarranted inflammatory responses that follow tissue damage, thus facilitating a conducive environ for automatic tissue repair; and (b) produce proteins that kill bacteria like Escherichia coli and Staphylococcus aureus and thus enhancing microbial clearance from the body systems. In view of the aforementioned diverse functions of dermal papilla cells, it is important to maintain the healthy state of these cells in terms of numbers and morphology and also protect their stem cell characteristics.

The ability of selenopeptides gamma-L-glutamyl-Selenomethyl-L-selenocysteine and γ-L-glutamyl-L-Selenomethionine to enhance vascular endothelial growth factor (VEGF) and its 5-alpha reductase activity was documented in US8003614 (Majeed et al.). Surprisingly, the present inventors note that selenopeptides though being poor protectants of dermal papilla cells by themselves, synergistically enhance the dermal papilla protective ability of the formulations disclosed by Majeed et al. in US 20110033565, said formulations comprising compositions that include (a) 1-O-galloyl-β-D-glucose (β-glucogallin) or β-glucogallin and gallates, and (b) concentrate of liquid endosperm of Cocos nucifera.

As a result, synergistic selenopeptide formulations of the present invention find considerable application in maintaining morphologically healthy dermal papilla cells in sufficient numbers and thereby protecting the stem cell characteristics of the same.

It is the principle objective of the present invention to disclose protective formulations comprising synergistic compositions that include (a) β-glucogallin or β-glucogallin and gallates, (b) concentrate of liquid endosperm of Cocos nucifera and (c) selenopeptides that protect dermal papilla cells from stress signals and associated applications thereof.

The present invention fulfills the stated objective and provides further related advantages.

SUMMARY OF THE INVENTION

The present invention discloses formulations comprising synergistic compositions including (a) β-glucogallin or β-glucogallin and gallates (b) concentrate of liquid endosperm of Cocos nucifera and (c) selenopeptides for the protection of dermal papilla cells from stress signals.

Figure 1:
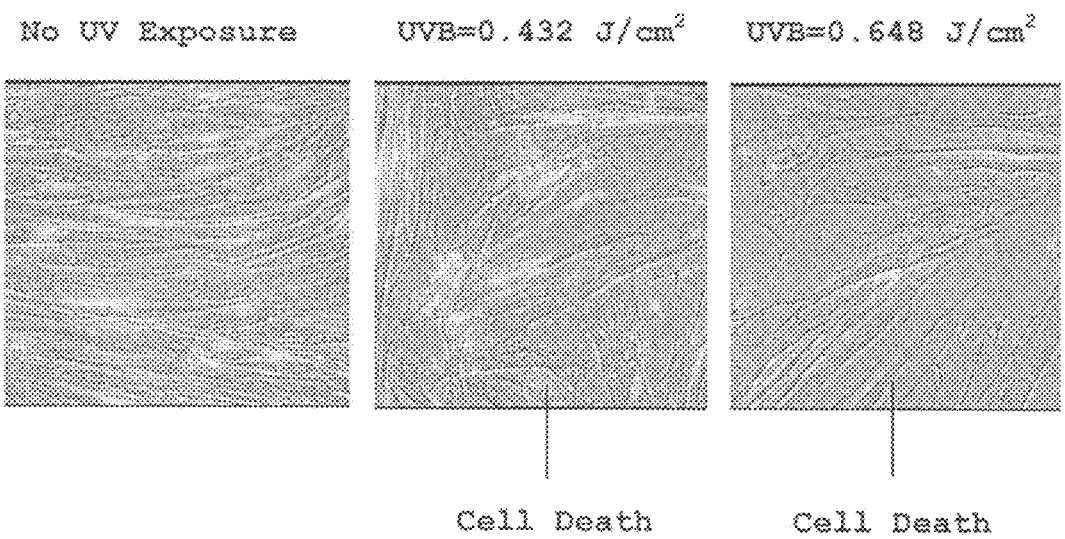
FIG. 1 shows the photomicrographs of 0.5% concentrate of liquid endosperm of Cocos nucifera, said concentrate comprising not less than 40% w/w of total dissolved solids unable to protect dermal papilla cells singly.

PC-8 provides significant (95%) protection to dermal papilla cells exposed to very high doses of UVB radiation of 1.0 J/cm$^2$.

FIG. 10 shows the photomicrographs of UVB irradiated dermal papilla cells treated with protective formulation PC-9 (0.001% w/w of γ-L-glutamyl-Selenomethyl-L-selenocysteine (FIG. 10a) or 0.001% w/w of γ-L-glutamyl-L-Selenomethionine (FIG. 10b)). PC-9 provides no protection to dermal papilla cells exposed to even low level of UVB radiation (UVB dose of 0.432 J/cm$^2$).

DESCRIPTION OF THE INVENTION

The present invention relates to dermal papilla cell protective formulation comprising synergistic composition, said composition including 1-O-galloyl-β-D-glucose (β-glucogallin), concentrate of liquid endosperm of *Cocos nucifera* and selenopeptides.

In another embodiment of the invention, the synergistic composition comprises at least 10% w/w of 1-O-galloyl-β-D-glucose (β-glucogallin).

In yet another embodiment of the invention, the synergistic composition comprises 0.5% w/w of the concentrate from the liquid endosperm of *Cocos nucifera*, said concentrate comprising not less than 40% w/w of total dissolved solids.

In still another embodiment of the invention, the synergistic composition comprises 0.001% w/w of selenopeptides.

In still another embodiment of the invention, the selenopeptide is γ-L-glutamyl-Selenomethyl-L-selenocysteine.

In still another embodiment of the invention, the selenopeptide is γ-L-glutamyl-L-Selenomethionine.

The present invention relates to dermal papilla cell protective formulation comprising synergistic composition, said composition including 1-O-galloyl-β-D-glucose (β-glucogallin) and gallates, concentrate of liquid endosperm of *Cocos nucifera* and selenopeptides.

In still another embodiment of the invention, the synergistic composition comprises at least 10% w/w of 1-O-galloyl-β-D-glucose (β-glucogallin) and 50% to greater than 50% total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid.

In still another embodiment of the invention, the synergistic composition comprises 0.5% w/w of the concentrate from the liquid endosperm of *Cocos nucifera*, said concentrate comprising not less than 40% w/w of total dissolved solids.

In still another embodiment of the invention, the synergistic composition comprises 0.001% w/w of selenopeptides.

In still another embodiment of the invention, the selenopeptide is γ-L-glutamyl-Selenomethyl-L-selenocysteine.

In still another embodiment of the invention, the selenopeptide is γ-L-glutamyl-L-Selenomethionine.

The present invention also relates to a method of increasing the tolerance of dermal papilla cells to stress signals, said method comprising step of bringing into contact the dermal papilla cells and the protective formulations as claimed in claims 1 or 7.

The present invention also relates to a method of maintaining the morphology and numbers of dermal papilla cells during exposure to stress signals, said method comprising step of bringing into contact the dermal papilla cells and the protective formulation as claimed in claims 1 or 7.

In still another embodiment of the invention, the dermal papilla cells include dermal stem/progenitor cells.

In the most preferred embodiment, the present invention relates to the following synergistic selenopeptide formulations for the protection of dermal papilla cells.

(A) PC-5 comprising synergistic compositions, said compositions including (a) 1-O-galloyl-β-D-glucose (β-glucogallin); (b) concentrate of liquid endosperm of *Cocos nucifera*, said concentrate including at least 40% dissolved solids and (c) γ-L-glutamyl-Selenomethyl-L-selenocysteine. In specific embodiments, said compositions comprise (a) at least 10% w/w 1-O-galloyl-β-D-glucose (β-glucogallin); (b) 0.5% w/w concentrate of liquid endosperm of *Cocos nucifera*, said concentrate including at least 40% dissolved solids; and (c) 0.001% w/w of γ-L-glutamyl-Selenomethyl-L-selenocysteine.

(B) PC-6 comprising synergistic compositions, said compositions including (a) 1-O-galloyl-β-D-glucose (β-glucogallin); (b) concentrate of liquid endosperm of *Cocos nucifera*, said concentrate including at least 40% dissolved solids and (c) γ-L-glutamyl-L-Selenomethionine. In specific embodiments, said compositions comprise (a) at least 10% w/w 1-O-galloyl-β-D-glucose (β-glucogallin); (b) 0.5% w/w of concentrate of liquid endosperm of *Cocos nucifera*, said concentrate including at least 40% dissolved solids; and (c) 0.001% w/w of γ-L-glutamyl-L-Selenomethionine.

(C) PC-7 comprising synergistic compositions, said compositions including, (a) 1-O-galloyl-β-D-glucose (β-glucogallin) and gallates; (b) concentrate of liquid endosperm of *Cocos nucifera*, said concentrate including at least 40% dissolved solids; and (c) γ-L-glutamyl-Selenomethyl-L-selenocysteine. In specific embodiments, said compositions comprise (a) at least 10% w/w of 1-O-galloyl-β-D-glucose (β-glucogallin) and 50% to greater than 50% w/w of total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid; (b) 0.5% w/w of concentrate of liquid endosperm of *Cocos nucifera*, said concentrate including at least 40% dissolved solids and (c) 0.001% w/w of γ-L-glutamyl-Selenomethyl-L-selenocysteine.

(D) PC-8 comprising synergistic compositions, said compositions including, (a) 1-O-galloyl-β-D-glucose (β-glucogallin) and gallates; (b) concentrate of liquid endosperm of *Cocos nucifera*, said concentrate including at least 40% dissolved solids; and (c) γ-L-glutamyl-L-Selenomethionine. In specific embodiments, said compositions comprise (a) at least 10% w/w of 1-O-galloyl-β-D-glucose (β-glucogallin) and 50% to greater than 50% w/w of total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid; (b) 0.5% w/w concentrate of liquid endosperm of *Cocos nucifera*, said concentrate including at least 40% dissolved solids and (c) 0.001% w/w of γ-L-glutamyl-L-Selenomethionine.

In other preferred embodiments of the invention, other dipeptides occurring as combinations with other amino acids may be used in the aforesaid synergistic dermal papilla cell protective formulations.

In an alternate embodiment, the present invention also relates to a method of increasing the tolerance of dermal papilla cells to stress signals, said method comprising step of bringing into contact dermal papilla cells and the protective formulation PC-5 comprising synergistic compositions, said compositions including, (a) 1-O-galloyl-β-D-glucose (β-glucogallin); (b) concentrate of liquid endosperm of *Cocos nucifera*, said concentrate including at least 40% dissolved solids and (c) γ-L-glutamyl-Selenomethyl-L-selenocysteine. In specific embodiments, said compositions comprise (a) at least 10% w/w of 1-O-galloyl-β-D-glucose (β-glucogallin); (b) 0.5% w/w concentrate of liquid endosperm of *Cocos nucifera*, said concentrate including at least 40% dissolved solids; and (c) 0.001% w/w of γ-L-glutamyl-Selenomethyl-L-selenocysteine.

In another alternative embodiment, the present invention also relates to a method of increasing the tolerance of dermal papilla cells to stress signals, said method comprising step of bringing into contact dermal papilla cells and the protective formulation PC-6 comprising synergistic compositions, said compositions including, (a) 1-O-galloyl-β-D-glucose (β-glucogallin); (b) concentrate of liquid endosperm of *Cocos nucifera*, said concentrate including at least 40% dissolved solids and (c) γ-L-glutamyl-L-Selenomethionine. In specific embodiments, said compositions comprise (a) at least 10% w/w of 1-O-galloyl-β-D-glucose (β-glucogallin); (b) 0.5% w/w concentrate of liquid endosperm of *Cocos nucifera*, said concentrate including at least 40% dissolved solids; and (c) 0.001% w/w of γ-L-glutamyl-L-Selenomethionine.

In another alternative embodiment, the present invention also relates to a method of increasing the tolerance of dermal papilla cells to stress signals, said method comprising step of bringing into contact dermal papilla cells and protective formulation PC-7 comprising synergistic compositions, said compositions including, (a) 1-O-galloyl-β-D-glucose (β-glucogallin) and gallates; (b) concentrate of liquid endosperm of *Cocos nucifera*, said concentrate including at least 40% dissolved solids; and (c) γ-L-glutamyl-Selenomethyl-L-selenocysteine. In specific embodiments, said compositions comprise (a) at least 10% w/w of 1-O-galloyl-β-D-glucose (β-glucogallin) and 50% w/w to greater than 50% w/w of total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid; (b) 0.5% w/w concentrate of liquid endosperm of *Cocos nucifera*, said concentrate including at least 40% dissolved solids and (c) 0.001% w/w of γ-L-glutamyl-Selenomethyl-L-selenocysteine.

In another alternative embodiment, the present invention also relates to a method of increasing the tolerance of dermal papilla cells to stress signals, said method comprising step of bringing into contact dermal papilla cells and protective formulation PC-8 comprising of synergistic compositions, said compositions including, (a) 1-O-galloyl-β-D-glucose (β-glucogallin) and gallates; (b) concentrate of liquid endosperm of *Cocos nucifera*, said concentrate including at least 40% dissolved solids; and (c) γ-L-glutamyl-L-Selenomethionine. In specific embodiments, said compositions comprise (a) at least 10% w/w of 1-O-galloyl-β-D-glucose (β-glucogallin) and 50% w/w to greater than 50% w/w of total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid; (b) 0.5% w/w concentrate of liquid endosperm of *Cocos nucifera*, said concentrate including at least 40% dissolved solids and (c) 0.001% w/w of γ-L-glutamyl-L-Selenomethionine.

In yet another alternative embodiment, the present invention also relates to a method of maintaining the morphology and numbers of dermal papilla cells during exposure to stress signals, said method comprising step of bringing into contact dermal papilla cells and the protective formulation PC-5 comprising synergistic compositions, said compositions including, (a) 1-O-galloyl-β-D-glucose (β-glucogallin); (b) concentrate of liquid endosperm of *Cocos nucifera*, said concentrate including at least 40% dissolved solids and (c) γ-L-glutamyl-Selenomethyl-L-selenocysteine. In specific embodiments, said compositions comprise (a) at least 10% w/w of 1-O-galloyl-β-D-glucose (β-glucogallin); (b) 0.5% w/w concentrate of liquid endosperm of *Cocos nucifera*, said concentrate including at least 40% dissolved solids; and (c) 0.001% w/w of γ-L-glutamyl-Selenomethyl-L-selenocysteine.

In yet another alternative embodiment, the present invention also relates to a method of maintaining the morphology and numbers of dermal papilla cells during exposure to stress signals, said method comprising step of bringing into contact dermal papilla cells and the protective formulation PC-6 comprising synergistic compositions, said compositions including, (a) 1-O-galloyl-β-D-glucose (β-glucogallin); (b) concentrate of liquid endosperm of *Cocos nucifera*, said concentrate including at least 40% dissolved solids and (c) γ-L-glutamyl-L-Selenomethionine. In specific embodiments, said compositions comprise (a) at least 10% w/w of 1-O-galloyl-β-D-glucose (β-glucogallin); (b) 0.5% w/w concentrate of liquid endosperm of *Cocos nucifera*, said concentrate including at least 40% dissolved solids; and (c) 0.001% w/w of γ-L-glutamyl-L-Selenomethionine.

In another alternative embodiment, the present invention also relates to a method of maintaining morphology and numbers of dermal papilla cells during exposure to stress signals, said method comprising step of bringing into contact dermal papilla cells and protective formulation PC-7 comprising synergistic compositions, said compositions including, (a) β-glucogallin and gallates; (b) concentrate of liquid endosperm of *Cocos nucifera*, said concentrate including at least 40% dissolved solids; and (c) γ-L-glutamyl-Selenomethyl-L-selenocysteine. In specific embodiments, said compositions comprise (a) at least 10% w/w of 1-O-galloyl-β-D-glucose (β-glucogallin) and 50% w/w to greater than 50% w/w of total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid; (b) 0.5% w/w concentrate of liquid endosperm of *Cocos nucifera*, said concentrate including at least 40% dissolved solids and (c) 0.001% w/w of γ-L-glutamyl-Selenomethyl-L-selenocysteine.

In another alternative embodiment, the present invention also relates to a method of maintaining the morphology and viable numbers of dermal papilla cells during exposure to stress signals, said method comprising step of bringing into contact dermal papilla cells and protective formulation PC-8 comprising of synergistic compositions, said compositions including, (a) β-glucogallin and gallates; (b) concentrate of liquid endosperm of *Cocos nucifera*, said concentrate including at least 40% dissolved solids; and (c) γ-L-glutamyl-L-Selenomethionine. In specific embodiments, said compositions comprise (a) at least 10% w/w of 1-O-galloyl-β-D-glucose (β-glucogallin) and 50% w/w to greater than 50% w/w of total gallates including mucic acid 1,4-lactone-5-O-gallate, mucic acid 2-O-gallate, mucic acid 6-methyl ester 2-O-gallate, mucic acid 1-methyl ester 2-O-gallate and ellagic acid; (b) 0.5% w/w concentrate of liquid endosperm of *Cocos nucifera*, said concentrate including at least 40% dissolved solids and (c) 0.001% w/w of γ-L-glutamyl-L-Selenomethionine.

In a more specific embodiment, the dermal papilla cells mentioned herein above comprise dermal stem/progenitor cells.

Example I

General Procedure

Human dermal papilla cells were plated into a 96 well flat bottomed clear micro plate at a seeding density of 5000 cells per well. The 24 hour monolayer of cells was exposed to UVB dosages ranging from 0.0072 J/cm$^2$ to 1.0 J/cm$^2$ (stress signal) with or without sample (protective formulations) treatment. After exposure, the cells were incubated in a CO$_2$ incubator for 48 hours and developed by NRU (Neutral Red Uptake) staining techniques to analyze cell viability. The absorbance due to viable cells is read at 492 nm in a micro plate reader.

Sample tested—0.5% concentrate of liquid endosperm of Cocos nucifera, said concentrate comprising not less than 40% w/w of total dissolved solids.

FIG. 1 shows that the 0.5% concentrate of liquid endosperm of Cocos nucifera, said concentrate comprising not less than 40% w/w of total dissolved solids is unable to protect dermal papilla cells singly at 0.43 J/cm$^2$ and 0.648 J/cm$^2$ UVB exposure levels.

Sample tested: PC-1 in comparison with UVB irradiated untreated cells.

Figure 2:
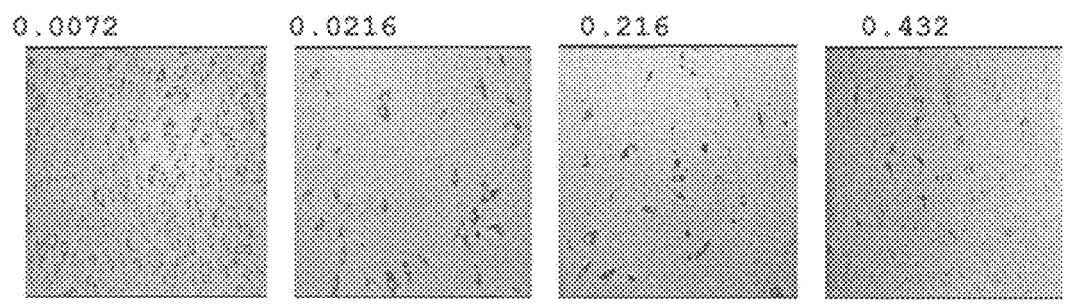
FIG. 2 shows the photomicrographs of UVB irradiated dermal papilla cells treated with protective formulation PC-1 (compositions comprising at least 10% w/w of 1-O-galloyl-β-D-glucose (β-glucogallin) in comparison with UVB irradiated untreated cells. PC-1 is unable to protect dermal papilla cells from UVB dosage above 0.43 $J/cm^2$. Cell damage in PC-1 treated cells occurs at UVB dosage of 0.648 $J/cm^2$ (shown as part of FIG. 4).
Figure 2:
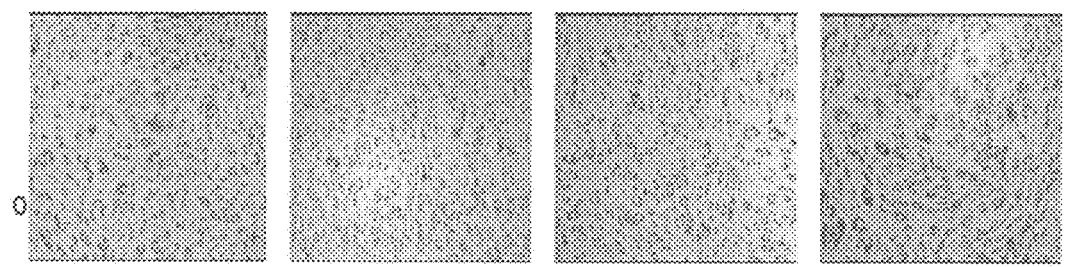

FIG. 2 shows PC-1 by itself is able to protect dermal papilla cells from UVB exposure levels of only up to 0.43 J/cm$^2$.

Sample tested: PC-2 in comparison with UVB irradiated untreated cells.

Figure 3:
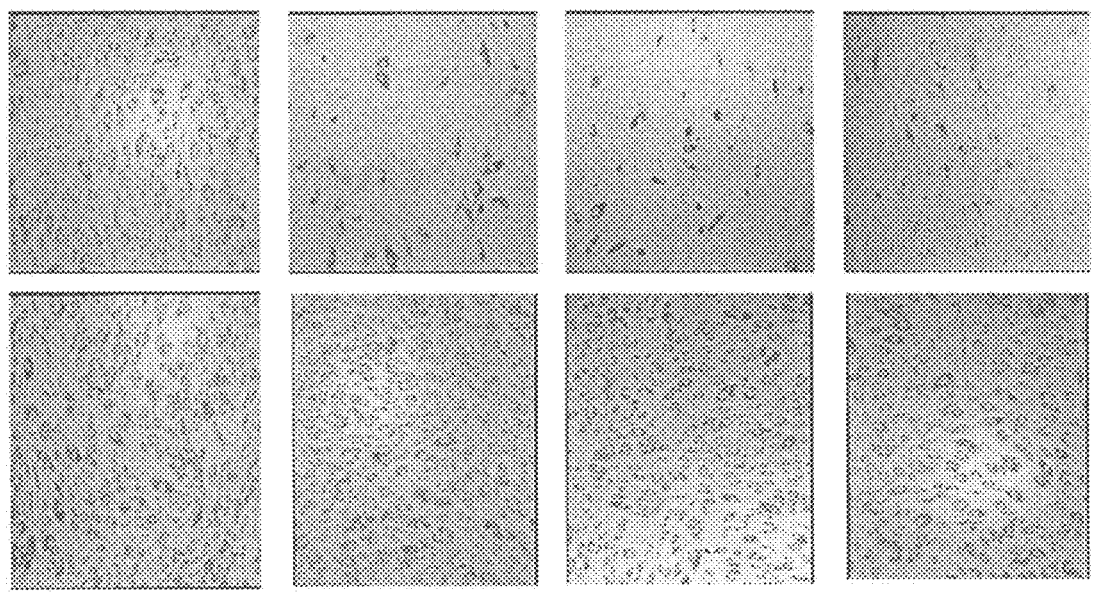
FIG. 3 shows the photomicrographs of UVB irradiated dermal papilla cells treated with protective formulation PC-2 (compositions comprising at least 10% w/w of 1-O-galloyl-β-D-glucose (β-glucogallin) and 50% to greater than 50% w/w of gallates) in comparison with UVB irradiated untreated cells. PC-2 is unable to protect dermal papilla cells from UVB dosage above 0.43 $J/cm^2$. Cell damage in PC-2 treated cells occurs at UVB dosage of 0.648 $J/cm^2$ (shown as part of FIG. 5).

FIG. 3 shows PC-2 by itself is able to protect dermal papilla cells from UVB exposure levels of only up to 0.43 J/cm$^2$.

Sample tested: PC-3

Figure 4:
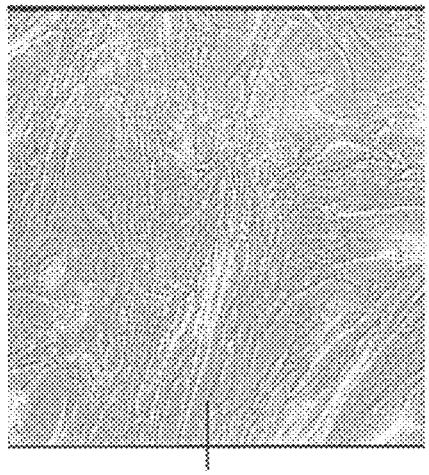
FIG. 4 shows the photomicrographs of UVB irradiated dermal papilla cells treated with protective formulation PC-3 (PC-1+0.5% concentrate of liquid endosperm of Cocos nucifera, said concentrate comprising not less than 40% w/w of total dissolved solids). PC-3 protects dermal papilla cells from UVB exposure levels of up to only 0.648 $J/cm^2$ and not 0.8 $J/cm^2$. Cell death at 0.8 $J/cm^2$ is shown in the figure.
Figure 4:
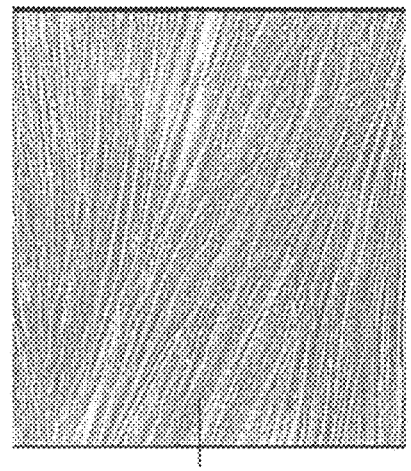
Figure 4:
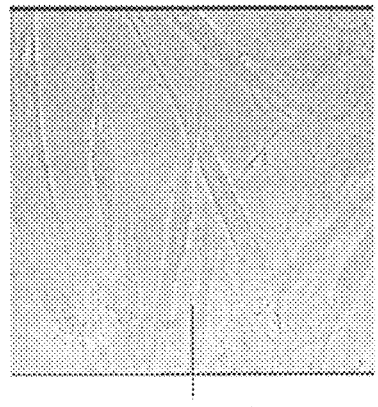

FIG. 4 shows that PC-3 is able to protect dermal papilla cells from UVB exposure levels of up to 0.648 J/cm$^2$ and death of PC-3 treated dermal papilla cells is seen at UVB exposure level of 0.8 J/cm$^2$.

Sample tested: PC-4.

Figure 5:
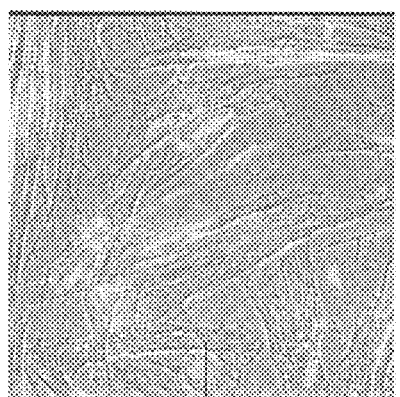
FIG. 5 shows the photomicrographs of UVB irradiated dermal papilla cells treated with protective formulation PC-4 (PC-2+0.5% concentrate of liquid endosperm of Cocos nucifera, said concentrate comprising not less than 40% w/w of total dissolved solids). PC-4 protects dermal papilla cells at UVB exposure levels of only up to 0.648 $J/cm^2$ and not 0.8 $J/cm^2$. Cell death at 0.8 $J/cm^2$ is shown in the figure.
Figure 5:
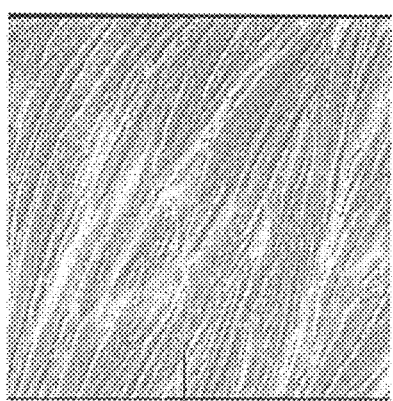
Figure 5:
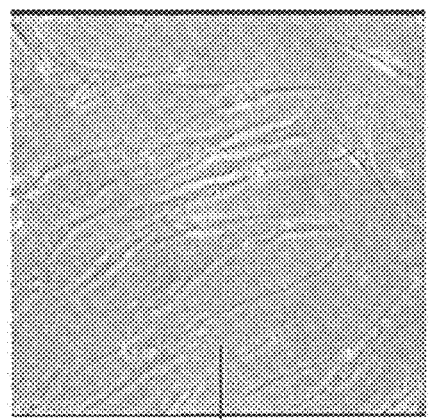

FIG. 5 shows that PC-4 is able to protect dermal papilla cells from UVB exposure levels of up to at 0.648 J/cm$^2$ UVB exposure levels and death of PC-4 treated dermal papilla cells is seen at UVB exposure level of 0.8 J/cm$^2$.

Sample tested-PC-9

FIG. 10 shows that neither γ-L-glutamyl-Selenomethyl-L-selenocysteine (FIG. 10a) nor γ-L-glutamyl-L-Selenomethionine (FIG. 10b) by themselves are able to protect dermal papilla cells even at low levels of UVB exposure (0.432 J/cm$^2$).

Sample tested: PC-5

Figure 6:
FIG. 6 shows the photomicrographs of UVB irradiated dermal papilla cells treated with protective formulation PC-5 (PC-3+0.001% w/w of γ-L-glutamyl-Selenomethyl-L-selenocysteine). PC-5 provides significant (95%) protection to dermal papilla cells exposed to UVB radiation of 0.8 $J/cm^2$.
Figure 6:
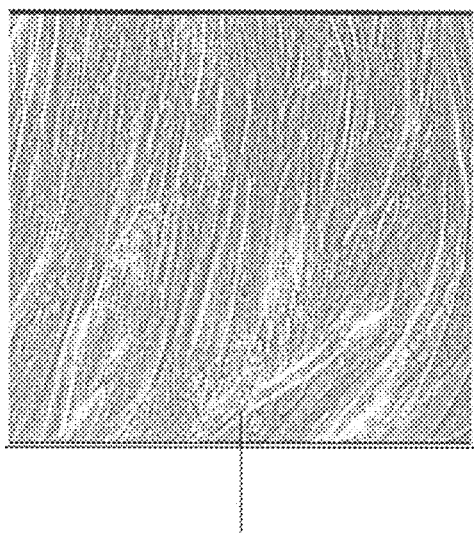

FIG. 6 shows that PC-5 provides significant (95%) protection to dermal papilla cells exposed to UVB radiation levels of 0.8 J/cm$^2$.

Sample tested: PC-6

Figure 7:
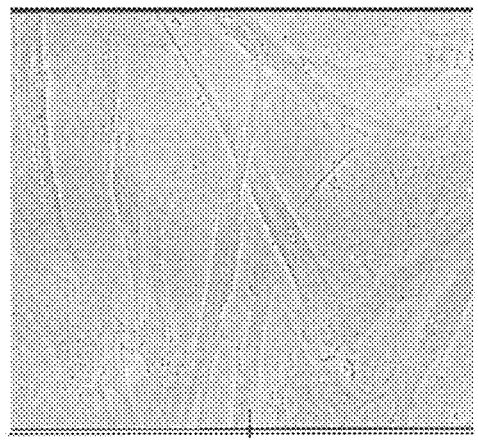
FIG. 7 shows the photomicrographs of UVB irradiated dermal papilla cells treated with protective formulation PC-6 (PC-3+0.001% w/w of γ-L-glutamyl-L-Selenomethionine). PC-6 provides significant (95%) protection to dermal papilla cells exposed to UVB radiation of 1.0 $J/cm^2$.
Figure 7:
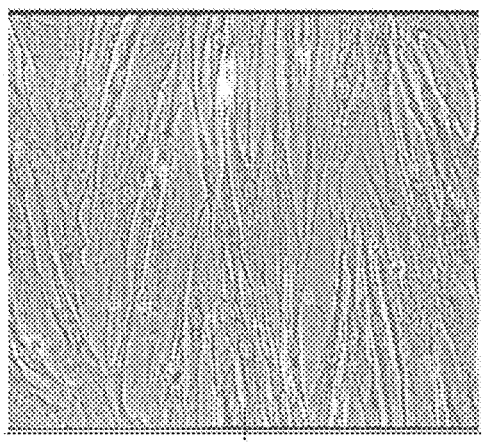

FIG. 7 shows that PC-6 provides significant (95%) protection to dermal papilla cells exposed to UVB radiation levels of 1.0 J/cm$^2$.

Sample tested: PC-7

Figure 8:
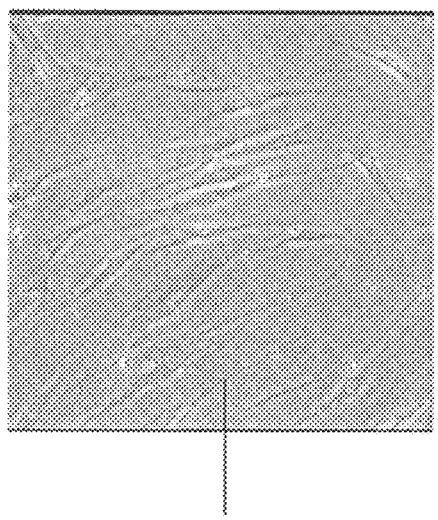
FIG. 8 shows the photomicrographs of UVB irradiated dermal papilla cells treated with protective formulation PC-7 (PC-4+0.001% w/w of γ-L-glutamyl-Selenomethyl-L-selenocysteine). PC-7 provides significant (95%) protection to dermal papilla cells exposed to UVB radiation of 0.8 $J/cm^2$.
Figure 8:
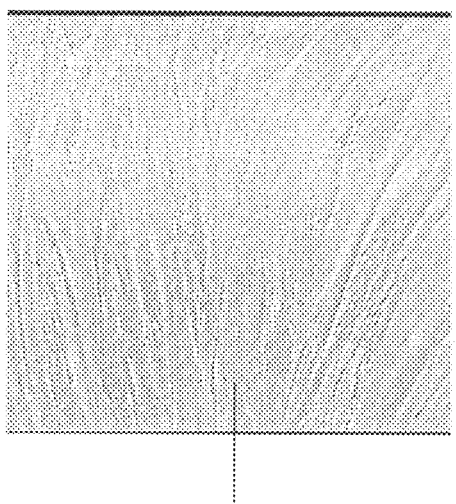

FIG. 8 shows that PC-7 provides significant (95%) protection to dermal papilla cells exposed to UVB radiation levels of 0.8 J/cm$^2$.

Sample tested: PC-8

Figure 9:
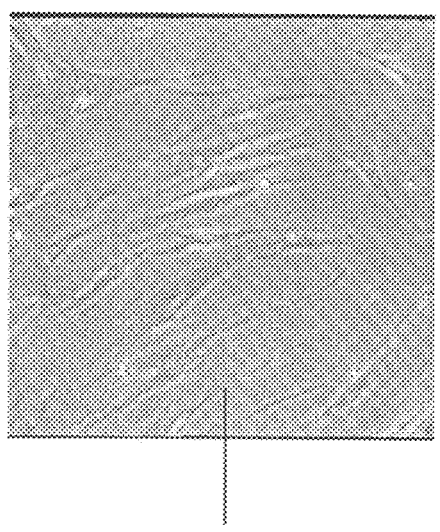
FIG. 9 shows the photomicrographs of UVB irradiated dermal papilla cells treated with protective formulation PC-8 (PC-4+0.001% w/w of γ-L-glutamyl-L-Selenomethionine).
Figure 9:
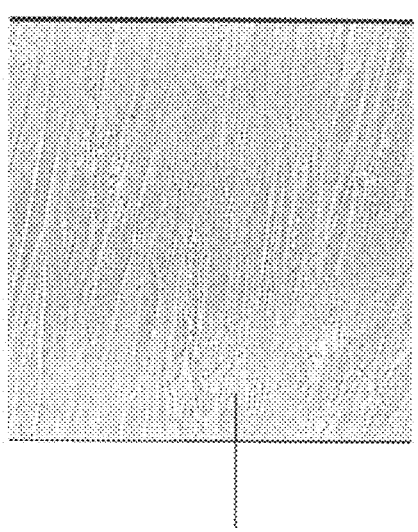

FIG. 9 shows that PC-8 provides significant (95%) protection to dermal papilla cells exposed to UVB radiation levels of 1.0 J/cm$^2$.

The effect of various samples used in the invention is presented herein below as Table 1.

TABLE 1

| Samples | UVB irradiation levels on dermal papilla cells | | |
|---|---|---|---|
| (Protective formulations tested) | 0.432 J/cm$^2$ | 0.648 J/cm$^2$ | 0.8 or 0.1 J/cm$^2$ |
| Concentrate of liquid endosperm of Cocos nucifera | No protection (cell death observed) | — | — |
| PC-1 Compositions comprising at least 10% w/w or greater of 1-O-galloyl-β-D-glucose (β-glucogallin) | Provides protection | No protection (Causes cell damage) | — |
| PC-2 Compositions comprising at least 10% w/w or greater of β-glucogallin and 50% w/w or greater than 50% w/w of gallates. | Provides protection | No protection (Causes cell damage) | — |
| PC-3 (PC-1 + concentrate of liquid endosperm of Cocos nucifera) | Provides protection | Provides protection | No protection |
| PC-4 (PC-2 + concentrate of liquid endosperm of Cocos nucifera) | Provides protection | Provides protection | No protection |
| γ-L-glutamyl-Selenomethyl-L-selenocysteine (PC-9) | No protection | — | — |
| γ-L-glutamyl-L-Selenomethionine (PC-9) | No protection | — | — |
| PC-5 (PC-3 + γ-L-glutamyl-Selenomethyl-L-selenocysteine) | Provides protection | Provides protection | Provides protection |
| PC-6 (PC-3 + γ-L-glutamyl-L-Selenomethionine) | Provides protection | Provides protection | Provides protection |
| PC-7 (PC-4 + γ-L-glutamyl-Selenomethyl-L-selenocysteine) | Provides protection | Provides protection | Provides protection |
| PC-8 (PC-4 + γ-L-glutamyl-L-Selenomethionine) | Provides protection | Provides protection | Provides protection |

From the results, it is evident that

A. The selenopeptides and concentrate of liquid endosperm of Cocos nucifera singly do not confer protection to dermal papilla cells at even low levels of UVB exposure (0.432 J/cm$^2$).

B. β-glucogallin or β-glucogallin and gallates are able to provide protection of dermal papilla cells only up to UVB exposure levels of 0.432 J/cm$^2$.

C. Although the combination of concentrate of liquid endosperm of Cocos nucifera and β-glucogallin or β-glucogallin and gallates provides protection to dermal papilla cells from UVB exposure levels up to 0.648

J/cm², said protection does not extend beyond this level. Rather, the tolerance level to the tested stress signal is 0.648 J/cm².

D. However, the combination of (a) β-glucogallin or β-glucogallin and gallates, (b) concentrate of liquid endosperm of *Cocos nucifera* and (c) selenopeptides extend protection to dermal papilla cells at UVB exposure levels even beyond 0.648 J/cm⁻², specifically between 0.8-1.0 J/cm². Selenopeptides though being poor protectants of dermal papilla cells by themselves, synergistically enhance the dermal papilla cell protective ability of formulations comprising (a) 1-O-galloyl-β-D-glucose (β-glucogallin) or 1-O-galloyl-β-D-glucose (β-glucogallin) and gallates and (b) the concentrate of liquid endosperm of *Cocos nucifera*. Thus an unexpected improved tolerance of dermal papilla cells to stress signals conferred by the synergistic combination of (a) 1-O-galloyl-β-D-glucose (β-glucogallin) or 1-O-galloyl-β-D-glucose (β-glucogallin) and gallates, (b) concentrate of liquid endosperm of *Cocos nucifera* and (c) selenopeptides is clear from the instant invention. The composition of the present invention shows superior activity when compared to individual components or other combinations.

It is to be understood that though the present invention has been described with reference to specific preferred examples, it is possible for persons having ordinary skill in the art to make modifications and variations without departing from the spirit of the invention. Accordingly, the foregoing disclosure should be interpreted as illustrative only and not in a limiting sense. The present invention is limited only by the scope of appended claims which also includes the scope of equivalents.

We claim:

1. A method of increasing the tolerance of dermal papilla cells to stress signals, the method comprising:
    bringing into contact the dermal papilla cells and a formulation comprising a composition; wherein
        the composition comprises:
            1-O-galloyl-β-D-glucose,
            concentrate of liquid endosperm of *Cocos nucifera*, and
            0.001% w/w of a selenopeptide, the selenopeptide being selected from the group consisting of γ-L-glutamyl-selenomethyl-L-selenocysteine, and γ-L-glutamyl-selenomethyl-L-selenomethionine; and
        the formulation brings about the effect of maintaining the morphology and numbers of the dermal papilla cells when exposed to stress signals.

2. The method of claim 1, wherein the composition comprises 0.5% w/w of the concentrate from the liquid endosperm of *Cocos nucifera*, the concentrate comprising not less than 40% w/w of total dissolved solids.

3. The method of claim 1, wherein the composition comprises at least 10% w/w of 1-O-galloyl-β-D-glucose.

4. The method of claim 1, wherein the selenopeptide is γ-L-glutamyl-selenomethyl-L-selenocysteine.

5. The method of claim 1, wherein the selenopeptide is γ-L-glutamyl-selenomethyl-L-selenomethionine.

6. The method of claim 1, wherein the composition comprises:
    0.5% w/w of the concentrate from the liquid endosperm of *Cocos nucifera*, the concentrate comprising not less than 40% w/w of total dissolved solids,
    at least 10% w/w of 1-O-galloyl-β-D-glucose, and
    the selenopeptide is γ-L-glutamyl-selenomethyl-L-selenocysteine.

7. The method of claim 1, wherein the composition comprises:
    0.5% w/w of the concentrate from the liquid endosperm of *Cocos nucifera*, the concentrate comprising not less than 40% w/w of total dissolved solids,
    at least 10% w/w of 1-O-galloyl-β-D-glucose, and
    the selenopeptide is γ-L-glutamyl-selenomethyl-L-selenomethionine.

8. The method of claim 1, wherein the stress signals are UVB radiation levels, and the numbers of live dermal papilla cells are maintained at a level of 95% or more when the dermal papilla cells are exposed to UVB radiation levels are in the range of from 0.648 J/cm² to 1.0 J/cm².

9. The method of claim 1, wherein the stress signals are UVB radiation levels, and the numbers of live dermal papilla cells are maintained at a level of 95% or more when the dermal papilla cells are exposed to UVB radiation levels are in the range of from 0.8 J/cm² to 1.0 J/cm².

10. A method of increasing the tolerance of dermal papilla cells to stress signals, the method comprising:
    bringing into contact the dermal papilla cells and a formulation comprising a composition; wherein
        the composition comprises:
            1-O-galloyl-β-D-glucose,
            mucic acid gallates,
            concentrate of liquid endosperm of *Cocos nucifera*, and
            0.001% w/w of a selenopeptide, the sclenopeptide being selected from the group consisting of γ-L-glutamyl-selenomethyl-L-selenocysteine, and γ-L-glutamyl-selenomethyl-L-selenomethionine; and
        the formulation brings about the effect of maintaining the morphology and numbers of the dermal papilla cells when exposed to stress signals.

11. The method of claim 10, wherein the composition comprises 0.5% w/w of the concentrate from the liquid endosperm of *Cocos nucifera*, the concentrate comprising not less than 40% w/w of total dissolved solids.

12. The method of claim 10, wherein the composition comprises at least 10% w/w of 1-O-galloyl-β-D-glucose, and 50% w/w or greater total gallates.

13. The method of claim 10, wherein the selenopeptide is γ-L-glutamyl-selenomethyl-L-selenocysteine.

14. The method of claim 10, wherein the selenopeptide is γ-L-glutamyl-selenomethyl-L-selenomethionine.

15. The method of claim 10, wherein the composition comprises:
    0.5% w/w of the concentrate from the liquid endosperm of *Cocos nucifera*, the concentrate comprising not less than 40% w/w of total dissolved solids,
    at least 10% w/w of 1-O-galloyl-β-D-glucose,
    50% w/w or greater of total gallates selected from mucic acid 1,4-lactone-5-O-gallate, mucic acid 2-O-gallate, mucic acid 6-methyl ester 2-O-gallate, mucic acid 1-methyl ester 2-O-gallate and ellagic acid, and
    the selenopeptide is γ-L-glutamyl-selenomethyl-L-selenocysteine.

16. The method of claim 10, wherein the composition comprises:
    0.5% w/w of the concentrate from the liquid endosperm of *Cocos nucifera*, the concentrate comprising not less than 40% w/w of total dissolved solids,
    at least 10% w/w of 1-O-galloyl-β-D-glucose, 50% w/w or greater of total gallates selected from mucic acid 1,4-lactone-5-O-gallate, mucic acid 2-O-gallate, mucic acid 6-methyl ester 2-O-gallate, mucic acid 1-methyl ester 2-O-gallate and ellagic acid, and the selenopeptide is γ-L-glutamyl-selenomethyl-L-selenomethionine.

17. The method of claim 10, wherein the stress signals are UVB radiation levels, and the numbers of live dermal papilla cells are maintained at a level of 95% or more when the dermal papilla cells are exposed to UVB radiation levels are in the range of from 0.648 J/cm$^2$ to 1.0 J/cm$^2$.

18. The method of claim 10, wherein the stress signals are UVB radiation levels, and the numbers of live dermal papilla cells are maintained at a level of 95% or more when the dermal papilla cells are exposed to UVB radiation levels are in the range of from 0.8 J/cm$^2$ to 1.0 J/cm$^2$.

\* \* \* \* \*